United States Patent
Gminder

(12) 
(10) Patent No.: US 6,245,069 B1
(45) Date of Patent: Jun. 12, 2001

(54) CUTTING LOOP ELECTRODE FOR HIGH-FREQUENCY INSTRUMENT

(75) Inventor: Frank Gminder, Trossingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/320,316

(22) Filed: May 26, 1999

Related U.S. Application Data

(63) Continuation-in-part of application No. 09/091,119, filed on Sep. 12, 1998.

(51) Int. Cl.[7] .................................................. A61B 18/18
(52) U.S. Cl. .................................. 606/47; 606/46; 606/45
(58) Field of Search .......................... 606/46, 47, 41, 606/45

(56) References Cited

U.S. PATENT DOCUMENTS

| | | | |
|---|---|---|---|
| 5,782,829 | * | 7/1998 | Swaintek et al. ...................... 606/46 |
| 5,919,190 | * | 7/1999 | VanDusseldorp ...................... 606/46 |
| 5,957,923 | * | 9/1999 | Hahnen et al. ........................ 606/46 |
| 6,033,400 | * | 3/2000 | Grossi et al. .......................... 606/41 |
| 6,080,152 | * | 6/2000 | Nardella et al. ...................... 606/46 |

FOREIGN PATENT DOCUMENTS

| | | |
|---|---|---|
| 2521719 | 11/1976 | (DE) . |
| 295 19 844 | 3/1996 | (DE) . |
| 825301 | 3/1938 | (FR) . |

* cited by examiner

*Primary Examiner*—Linda C. M. Dvorak
*Assistant Examiner*—Roy Gibson
(74) *Attorney, Agent, or Firm*—St. Onge Steward Johnston & Reens LLC

(57) ABSTRACT

A high frequency electrode to be used for example in a resectoscope is provided. The electrode includes a sharp cutting edge and a lower coagulating surface which is curved or approximately curved to reduce irritation of tissue by the trailing edge and provides good possibilities to excavate tissue.

12 Claims, 3 Drawing Sheets

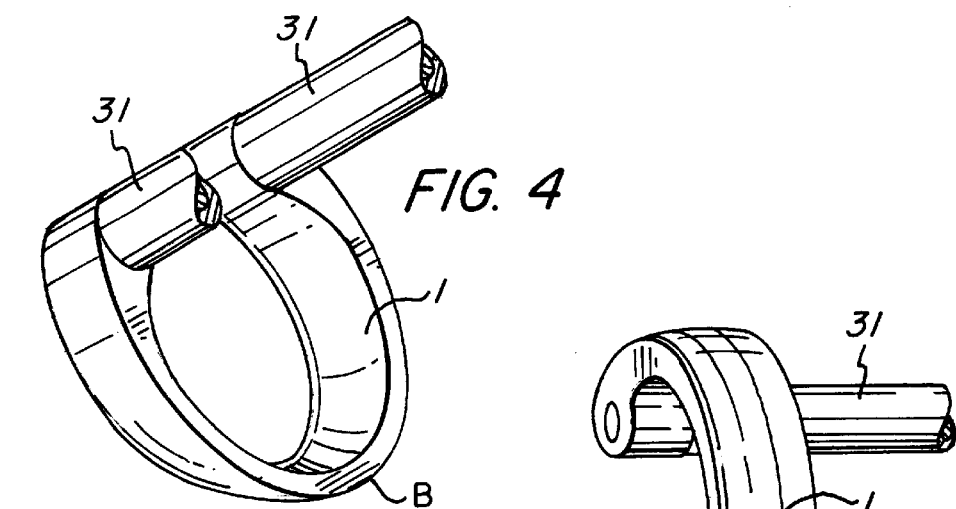
FIG. 4
FIG. 3
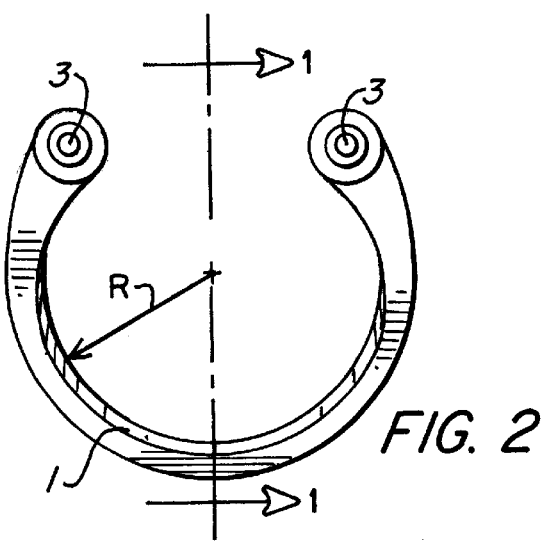
FIG. 2
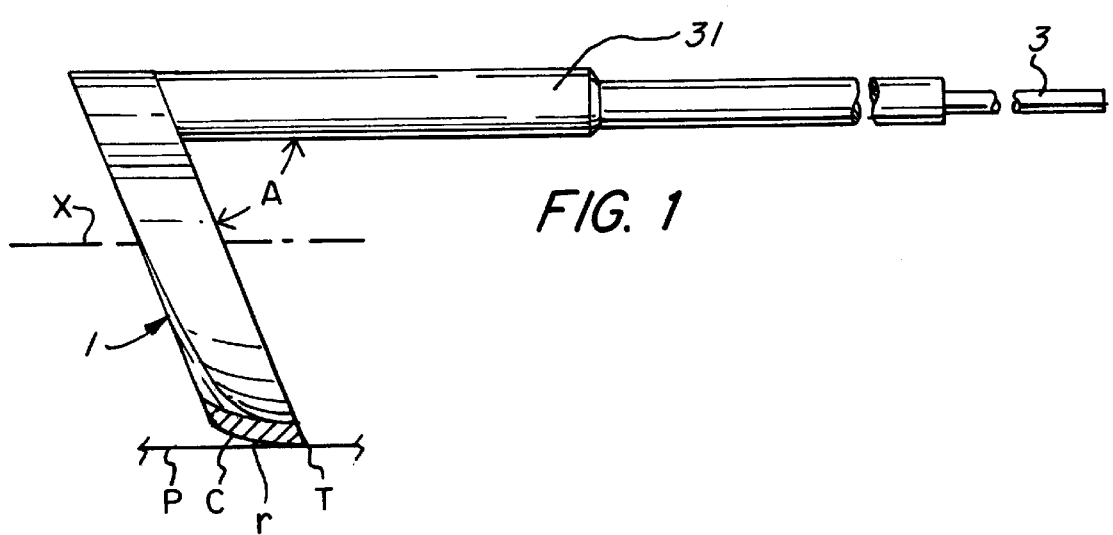
FIG. 1

CUTTING LOOP ELECTRODE FOR HIGH-FREQUENCY INSTRUMENT

This is a continuation-in-part U.S. application Ser. No. 09/091,119 filed Sep. 12, 1998.

FIELD OF THE INVENTION

The present invention relates to a loop electrode for a high-frequency instrument. Electrodes of this type are utilized, for example, in HF-resectoscopes.

BACKGROUND OF THE INVENTION

With conventional loop-shaped electrodes comprising a thin wire with a diameter of typical up to 1 mm or a corresponding flat material, incision and surface coagulation effects utilized for stanching the blood of cut blood vessels occur depending on the type of current—cutting mode, coagulation mode, spray coagulation mode—of the employed high-frequency generator.

The kind of current influences the "processing result": dependent on the applied current, in addition to the cutting effect, surface coagulation is generated which permits stanching the bleeding of blood vessels running near the surface.

Large area ball or roller electrodes to which "coagulation current" is applied usually are used only for large-area stanching of blood as the final step of the surgical procedure.

As an alternative for high-frequency tissue removal, lasers can be employed for tissue ablation. Lasers suited for this purpose are substantially more expensive than high-frequency generators, therefore attempts have been made to find ways to also be able to remove adinomatous tissue as bloodlessly as possible using a high-frequency generator.

A number of authors have suggested using conventional monopolar electrodes with a cylindrical roll. Reference is made to U.S. Pat. No. 5,395,363. The surface of the cylindrical roll can be designed in a variety of ways: rolls with smooth surfaces, with grooved surfaces or with pointed surfaces are known. However, using high-frequency electrodes with rolls has the drawback that the relatively large roll impedes the surgeon's vision. Secondly, it is only possible in practice to vaporize the tissue with such type rolls by supplying higher high-frequency power, efficiency being unsatisfactory. This means the patient is not only exposed to very high current flow respectively high energy, which involves potential risk, for considerable time, but also the narcosis time is distinctly longer than in other surgical techniques.

Cutting loop electrodes are also known. Reference is made to U.S. Pat. No. 5,569,244. Conventional cutting loops typically employ a single flat lower surface. By flat is meant that a plane P would intersect the loop lower surface S in a line L. In other words, as viewed from the side (see FIG. 5), or in cross section the loop exhibits a flat lower surface S. A drawback exists with this design in that a trailing edge E of the flat lower surface may increase irritation of the coagulated tissue.

SUMMARY OF THE INVENTION

The object of the present invention is to provide an electrode for a high-frequency instrument which vaporizes as well as cuts the tissue and with which surgery time is shortened and/or irritation of the coagulated tissue is reduced.

The invention relates to high-frequency electrodes having a sharpened cutting edge which permits optimized current flow from the cutting edge into the tissue upon incision. The high current density occurring at the edge leads to optimum incision into the tissue. As the invented electrodes essentially has the general shape of a loop, it does not impede the surgeon's vision at the surgical site.

An element of the present invention is that it was recognized that it is possible to vaporize as well as cut with an electrode with reduced irritation to coagulated tissue, if the electrode is provided with a curved and/or multiple flat lower, i.e., approximately curved surface portions. By "curved" is meant that a plane P would intersect loop lower surface C in a point T somewhere on the surface (depending upon inclination of the plane) since the surface is a complex curved surface (see FIG. 1). In other words, the electrode as viewed from the side or in cross section, exhibits a curved lower surface C. By "multiple flat" is meant that a plane P would intersect loop lower surface M in two or more lines L depending upon inclination of the plane (see FIG. 6A). In other words, the electrode as viewed from the side or in cross section exhibits a lower surface having two or more, and preferably having three or more flat surfaces M.

The invented electrodes permit simultaneous "bloodless" cutting and vaporizing of the tissue with a reduction in the irritation which might occur due to a dragging of the known electrode's single flat lower surface's trailing edge E over the coagulated tissue (see FIG. 5). On the basis of the inventive embodiment of a curved or multiple flat lower surface of the loop, high-frequency current flows into the tissue in a large surface and performs a coagulation and vaporization procedure during the cutting procedure. Nonetheless, it is still possible to "dig" respectively "excavate" to remove tissue with the invented electrode.

The selective application of the lateral stirrups to join the loop and lead or leads of the electrode provides advantages particular to conventional thin loop electrodes, notably removing respectively cutting off "parasol" sections of tissue.

In embodiment including stirrups, it is preferred if the stirrups do not comprise a wire material having a round cross section, but a band-shaped material respectively a material having an elliptical cross section, the longer axis of which extends in the direction of the longitudinal axis of the lead. In embodiments which desirably include stirrups, it is also generally preferred that the lead, the stirrups and the central section are arranged in a kind of "Z" configuration, facilitates cleaning the cut-off tissue from the invented electrodes.

The preferred dimensions of the cutting loop are a radius ® of about 3 mm at an angle (A) of about 60°. The radius of curvature ® of the lower surface is preferably about 2.5 mm.

The invented high-frequency electrode can be fabricated in a known manner and, in particular, can be made of high temperature resistant materials, in particular titanium alloys.

The top surface of the loop may be insulated in such a manner that current only flows through the bottom surface and cutting edge of the loop, thereby confining the current flow for vaporization and coagulation to the required region and reducing the patient's current load. The electrode trailing edge may also be insulated.

BRIEF DESCRIPTION OF THE DRAWINGS

The present invention is made more apparent in the following drawings of several embodiments, showing in:

FIG. 1 a side cross sectional view of a cutting loop embodiment of the invention including a preferred curved lower surface, FIG. 2 is an end elevation view of the cutting loop electrode of FIG. 1, FIG. 3 is a bottom plan view of the cutting loop electrode of FIG. 1, FIG. 4 is an isometric view of the cutting loop electrode of FIG. 1.

DETAILED DESCRIPTION OF THE INVENTION

Figure 6:
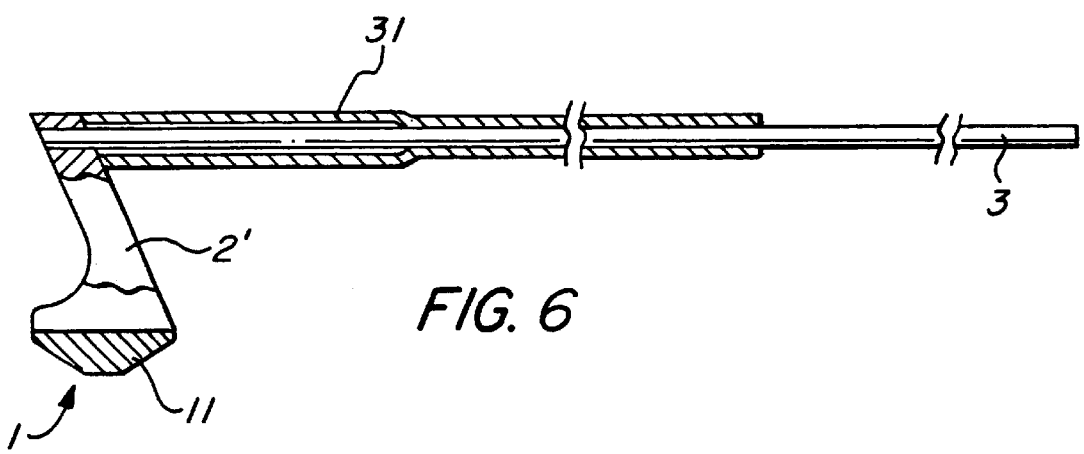
FIG. 6 is a side cross sectional view of a cutting loop embodiment of the invention including three lower flat surfaces and optional grooves on the lowermost flat surface.

FIG. 1 and 6 are diagrams of embodiments of the invented high-frequency electrode. The electrodes are provided with a central section 1, and in the FIG. 6 embodiment with two stirrups 2' and 2" joining the central section with an outside insulated lead 3, comprising two rods in the depicted embodiments. It is understood that a single rod may also be used. In the FIG. 1 embodiment, central section 1 extends and connects to leads 3, but stirrups may be used with this embodiment if desired.

The high-frequency electrode is connected via the outside insulated lead 3, for example, to a standard resectoscope (not depicted), which is connected to a high-frequency generator, also not depicted. This high-frequency generator is preferably a regulated generator. Instruments, such as those mass produced and sold by the applicant, Karl Storz GmbH & Co., Tuttlingen, Germany, can be used as resectoscopes and high-frequency generators.

Referring first to the preferred high frequency electrode, an embodiment of the invention illustrated in FIGS. 1–4 includes a curved lower surface C. The surface, as illustrated in FIG. 1, sweeps upwardly away from cutting edge E of the electrode. The curvature provides ample coagulation while reducing irritation caused by the trailing edge. The dimensions of the preferred electrode are a radius (R) of about 3 mm at an angle (A) of about 60°. The radius of curvature of the lower surface is about 2.5 mm. The remaining components of the FIG. 1 electrode are substantially the same as and are described with respect to FIGS. 6–8.

Figure 5:
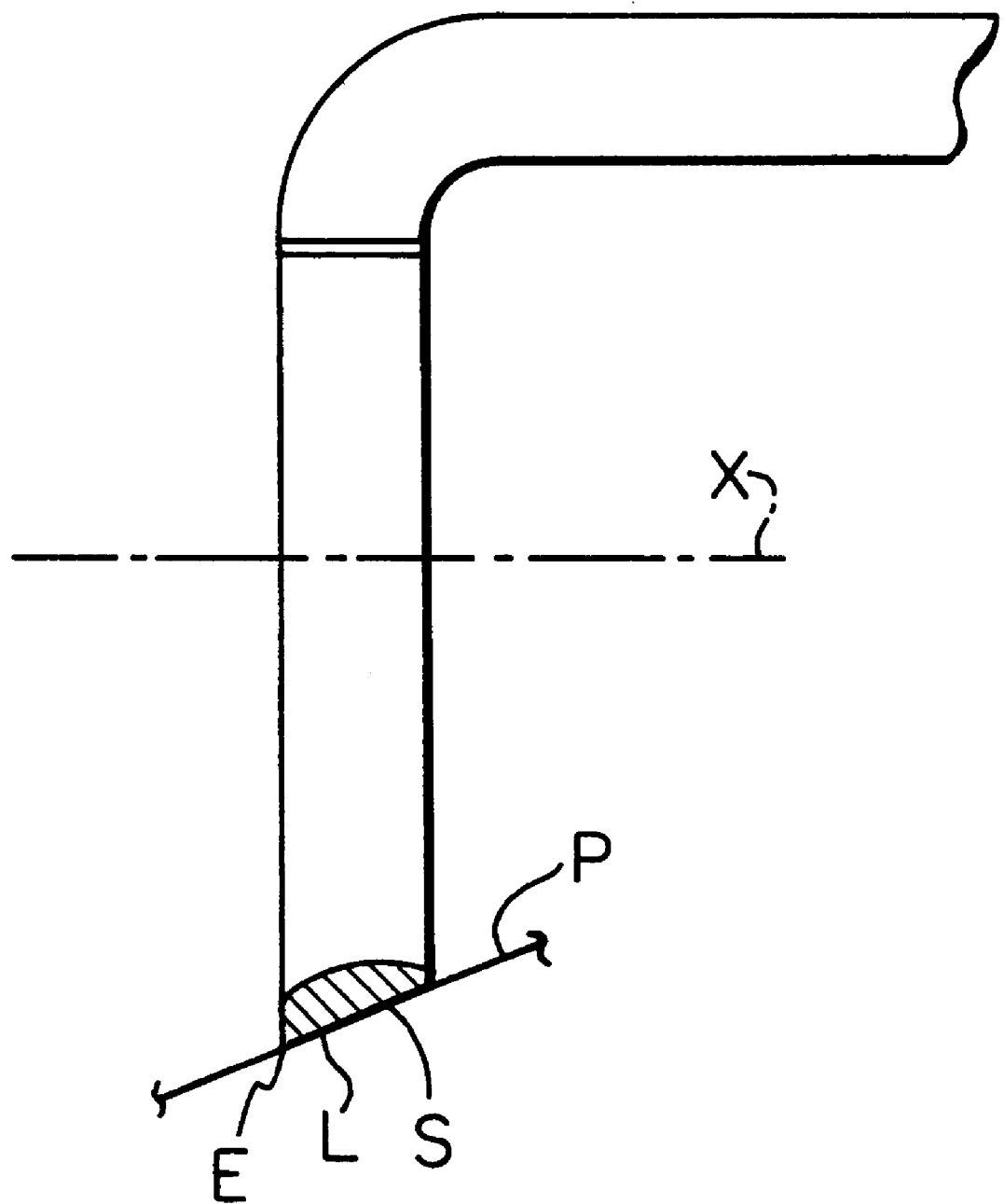
FIG. 5 is a side cross section view of a prior art cutting loop electrode having a single flat lower surface.
Figure 7:
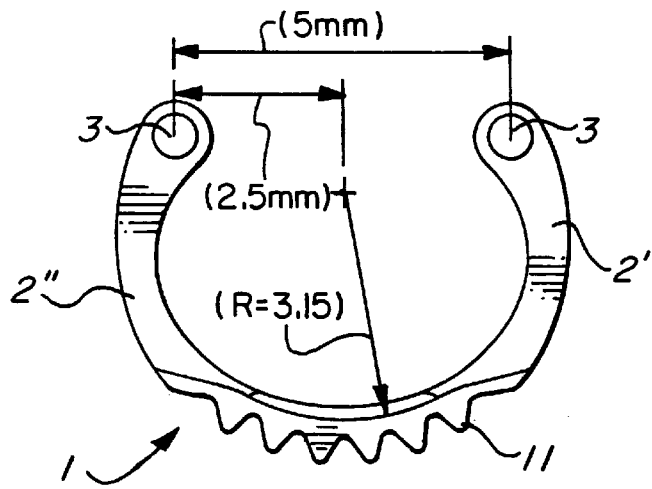
FIG. 7 is an end elevation view of the cutting loop electrode of FIG. 6.
Figure 8:
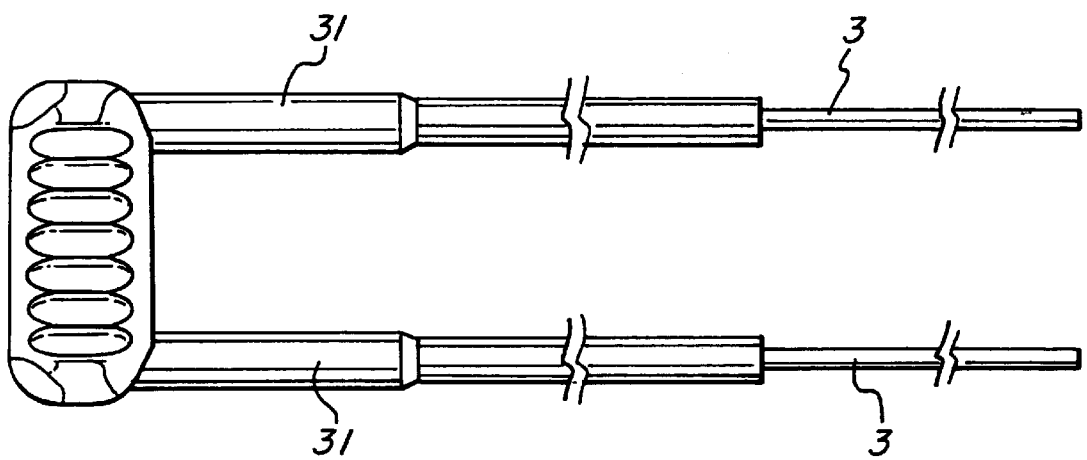
FIG. 8 is a bottom plan view of the cutting loop electrode of FIG. 6.

Referring now to FIGS. 6–8, the illustrated high frequency electrode has a lower surface comprised of three flat surfaces M. In contrast, the prior art cutting loop has only a single flat lower surface, and accordingly, the trailing edge E of the electrode may adversely irritate tissue. The triple flat lower surfaces of this embodiment of the invention, approximate the more preferred embodiment of the invention which includes a curved lower surface. The curved and approximately curved lower surface of a cutting loop electrode provide a high degree of coagulation and reduce irritation caused by a trailing edge of the known cutting loops illustrated in FIG. 5 and in U.S. Pat. No. 5,569,244.

The central section 1 of the high-frequency electrode has a longitudinal extension of about 0.6 to 1 mm for the loop of FIGS. 1–4, and about 2 mm to 6 mm, preferably 3 to 5 mm for the loop of FIGS. 6–8. The width of the central section 1 is typically about 5 mm.

The stirrups are made of a wire material or a band-shaped material having a diameter respectively an extension in the direction of the longitudinal axis X of the lead 3 of typically 1 mm, permitting in certain cases to also cut through the tissue with one of the stirrups.

Furthermore, the top side of the central section is provided with an insulation 4 and the bottom side may be provided with grooves as is illustrated in the FIG. 6 embodiment. By means of insulation 4, the current flow may be limited in that the current only enters the tissue from the bottom side but not from the top side of the central section.

In addition, the reference number 31 stands for an insulation of the leads and 11 for the grooves on the bottom side of the plate-shaped section 1. FIGS. 7 and 8 show the particularly preferred dimensions of the FIG. 6 embodiment. FIGS. 7 and 8 are executed using the same scale so that the other dimensions can be drawn from the figures.

The vaporization technique as well as the conventional cutting technique can be applied using the invented high-frequency electrode, thereby eliminating all the problems which can occur due to changing electrodes as required by the state of the art. Furthermore, the very high current flow, thus a current flow involving potential risk can be selectively employed only when it is really required. Simultaneous use of cutting and coagulation respectively vaporization methods makes the invented high-frequency electrode very efficient so that the narcosis times are distinctly shortened compare to other surgical methods.

What is claimed is:

1. A high-frequency electrode comprising:
   an insulated lead extending in the direction of a longitudinal axis of a high-frequency instrument, and
   an electrode component, electrically connected to said insulated lead, said electrode component having a central section, the central section having a cross section with a sharp cutting edge, a trailing edge, and a curved lower surface extending therebetween.

2. An electrode according to claim 1, characterized by that fact that stirrups are provided for connecting said central section to said insulated lead.

3. An electrode according to claim 1, characterized by the fact that a top side of said central section is provided with an insulation.

4. An electrode according to claim 1, characterized by the fact that said electrode is made of high temperature resistant materials, in particular of titanium alloys.

5. An electrode according to claim 1, characterized by the fact that the curved lower surface comprises a complex curved surface.

6. A high frequency electrode comprising
   an insulated lead extending in the direction of a longitudinal axis of a high frequency instrument, and
   an electrode component having a central section, a cross section of which is at least partially defined by a sharp cutting edge and a curved lower surface.

7. An electrode according to claim 6, characterized by that fact that stirrups are provided for connecting said central section to said insulated lead.

8. An electrode according to claim 7, characterized by the fact that said stirrups are made of a band shaped material.

9. An electrode according to claim 7, characterized by the fact that said lead, said stirrups and said central section are disposed in a kind of "Z".

10. An electrode according to claim 6, characterized by the fact that a top side of said central section is provided with an insulation.

11. An electrode according to claim 6, characterized by the fact that said electrode is made of high temperature resistant materials, in particular of titanium alloys.

12. An electrode according to claim 6, characterized by the fact that the curved lower surface comprises a complex curved surface.

* * * * *